United States Patent
Ladebeck et al.

[11] Patent Number: 5,936,404
[45] Date of Patent: Aug. 10, 1999

[54] NUCLEAR MAGNETIC RESONANCE TOMOGRAPHY APPARATUS WITH PRE-POLARIZATION

[75] Inventors: Ralf Ladebeck, Erlangen; Gregor Bett, Stuttgart, both of Germany

[73] Assignee: Siemens Aktiengesellschaft, Munich, Germany

[21] Appl. No.: 08/856,242

[22] Filed: May 14, 1997

[30] Foreign Application Priority Data

May 14, 1996 [DE] Germany ............................. 196 19 471

[51] Int. Cl.$^6$ ..................................... G01V 3/00
[52] U.S. Cl. ........................................ 324/300; 600/420
[58] Field of Search .................................. 324/300, 306, 324/307, 309, 312, 318, 322; 600/410, 420

[56] References Cited

U.S. PATENT DOCUMENTS

| | | | |
|---|---|---|---|
| 5,296,811 | 3/1994 | Ehnholm et al. | 324/319 |
| 5,545,396 | 8/1996 | Albert et al. | 424/93 |
| 5,798,921 | 8/1998 | Albert et al. | 324/300 |

OTHER PUBLICATIONS

"Novel Approaches to Low–Cost MRI," Macovski et al., Magnetic Resonance in Medicine, vol. 30 (1993), pp. 221–230.

"Magnetic Resonance Imaging Using Hyperpolized $^{129}$Xe," Albert et al., American Journal of Electromedicine, Dec. 1994, pp. 72–80.

"A Novel Double–Tuned Circuit for in Vivo NMR," Rajan et al., J. of Magnetic Resonance, vol. 74 (1987), pp. 147–154.

High–Power $^1$H–$^{19}$F Excitation in a Multiple–Resonance Single–Coil Circuit, Kendick et al., J. of Magnetic Resonance, vol. 75 (1987), pp. 506–508.

Primary Examiner—Louis Arana
Attorney, Agent, or Firm—Hill & Simpson

[57] ABSTRACT

In a nuclear magnetic resonance tomography apparatus wherein imaging is implemented with hyperpolarized gases, a first magnet system having a high field strength for the pre-polarization of the nuclear spins is provided. A gradient system for generating magnetic field gradients and a radio-frequency arrangement for the excitation of nuclear spins in a subject as well as for the read-out of the arising nuclear magnetic resonance signals are provided in a second magnet system having lower field strength.

9 Claims, 2 Drawing Sheets

NUCLEAR MAGNETIC RESONANCE TOMOGRAPHY APPARATUS WITH PRE-POLARIZATION

BACKGROUND OF THE INVENTION

1. Field of the Invention

The present invention is directed to a nuclear magnetic resonance tomography apparatus of the type having a first magnet system which produces a magnetic field having a first field strength for pre-polarization of the nuclear spins in an examination subject, and a second magnet system which produces a magnetic field having a second field strength that is significantly lower compared to the first field strength, with a gradient coil system for generating magnetic field gradients and a radio-frequency means for the excitation of nuclear spins as well as for the read-out of the arising nuclear magnetic resonance signals being allocated to the second magnet system.

2. Description of the Prior Art

A nuclear magnetic resonance tomography apparatus of the above type is disclosed, for example, in U.S. Pat. No. 5,296,811, as well as in A. Macovski, S. Conolly, "Novel Approaches To Low-Cost MRI" MRM 30: 221–230 (1993).

In a conventional nuclear magnetic resonance tomography apparatus, the nuclear spins are aligned in the direction of the magnetic field by a magnetic field produced by a magnet that accepts the body of the examination subject. The nuclear spins are excited by radio-frequency pulses and the arising nuclear magnetic resonance signals are read out in the same magnet system. A tomogram of the examination subject is subsequently reconstructed from the signals acquired in this way.

The magnet that is employed must have a comparatively high field strength so that an adequate signal-to-noise ratio is achieved. The signal strength of the nuclear magnetic resonance signal increases with increasing field strength. Typically, field strengths between 0.2 T and 4 T are employed.

Further, high demands are made with respect to the uniformity of the magnetic field, since spatial distortions and artifacts otherwise occur in the image that is acquired. In order to achieve the acquired homogeneity, magnets having a coil arrangement, which are typically implemented as superconductive magnets, must have a certain minimum structural length. If pole shoe magnets are used, a specific ratio of pole shoe diameter to pole shoe spacing cannot be downwardly transgressed for the same reason. Moreover, the required energy in the magnet increases with the spacing between the pole shoes.

Such magnets become extremely complicated due to the combination of the aforementioned conditions, namely, the combination of achieving high magnetic field strength with utmost uniformity. Typically, they represent by far the most expensive individual component of a nuclear magnetic resonance tomography system. Access to the patient during the examination is greatly limited in practice, further, because of the same demands. Pole shoe magnets, particularly according to the C-bend design, in fact allow significantly better access to the examined patient than do coil magnets. Due to the aforementioned conditions, however, the spacing between the pole shoes must be optimally small and the pole shoe surface must be made as large as possible, making interventional examinations more difficult.

One can manage with significantly simpler magnet arrangements when a pre-polarization of the examination subject is implemented, according to the aforementioned publications. In this case, the problem of the high field strength and the problem of high uniformity have been divided: a high field strength, namely, is only required for the pre-polarization but the demands made of the uniformity are relatively low since inhomogeneities are not expressed in local distortions or artifacts, but at most in terms of (correctable) image shadowings. The demands made of the uniformity are in fact high for the second magnet system in which the actual image acquisition ensues; however, one can manage with relatively low magnet field strengths since the signal-to-noise ratio is defined by the pre-polarization. Magnets that must satisfy only one of the demands with respect to uniformity or high field strength, however, can be built significantly more inexpensively. The aforementioned problems of accessibility can also be largely avoided.

Nuclear magnetic resonance tomography systems with pre-polarization, however, have not prevailed in practice, particularly since the image quality of conventional systems cannot be entirely achieved.

The reference, N. Albert et al., "Magnetic Resonance Imaging Using Hyperpolarized Xe", "American Journal Of Electro Medicine", December 1994, pgs. 72–80, discloses a method for MR imaging with hyperpolarized inert gases. The polarization does not occur on the basis of a strong magnetic field, but by laser-induced optical pumping. The hyperpolarized inert gas, for example $^{129}$Xe or $^{3}$He, is then administered to a patient by inhalation. The imaging occurs in a conventional nuclear magnetic resonance tomography apparatus. The high magnetic field of a classic nuclear magnetic resonance tomography apparatus thus not required at all, and is more likely to be disruptive due to its limited patient accessibility.

SUMMARY OF THE INVENTION

It is an object of the present invention to provide a nuclear magnetic resonance tomography apparatus of the type initially described wherein an improved cost/use relationship is achieved in conjunction with hyperpolarized gases.

The above object is achieved in accordance with the principles of the present invention in a nuclear magnetic resonance tomography apparatus having a first magnet system which produces a magnetic field having a first field strength for pre-polarization of nuclear spins in an examination subject, and a second magnet system which produces a magnetic field having a second field strength which is significantly lower than the first field strength, with a gradient system for generating magnetic field gradients and a radio frequency arrangement for exciting nuclear spins and for reading out the resulting nuclear magnetic resonance signals being allocated to the second magnet system, and further having an arrangement for supplying hyperpolarized gas to the examination subject with the radio frequency arrangement receiving nuclear magnetic resonance signals produced by the hyperpolarized gas.

Optimum accessibility to the examination subject is provided in an embodiment of the inventive nuclear magnetic resonance tomography apparatus wherein the second magnet system is composed of a Helmholtz arrangement having first and second coils respectively disposed above and below the examination subject, these coils being spaced from each other at a distance so that unimpeded access to the patient is provided. The coils of this magnet system can be respectively arranged, for example, in the ceiling and in the floor of an examination room containing the tomography apparatus.

In another embodiment, the apparatus is operated to allow for a time span between a beginning of inhalation of the hyperpolarized gas by the patient and image production, the gas having been at least partially absorbed by the body in this time span. This results in, for example, blood vessels can be very clearly recognizable in the resulting image.

DESCRIPTION OF THE PREFERRED EMBODIMENTS

Figure 1:
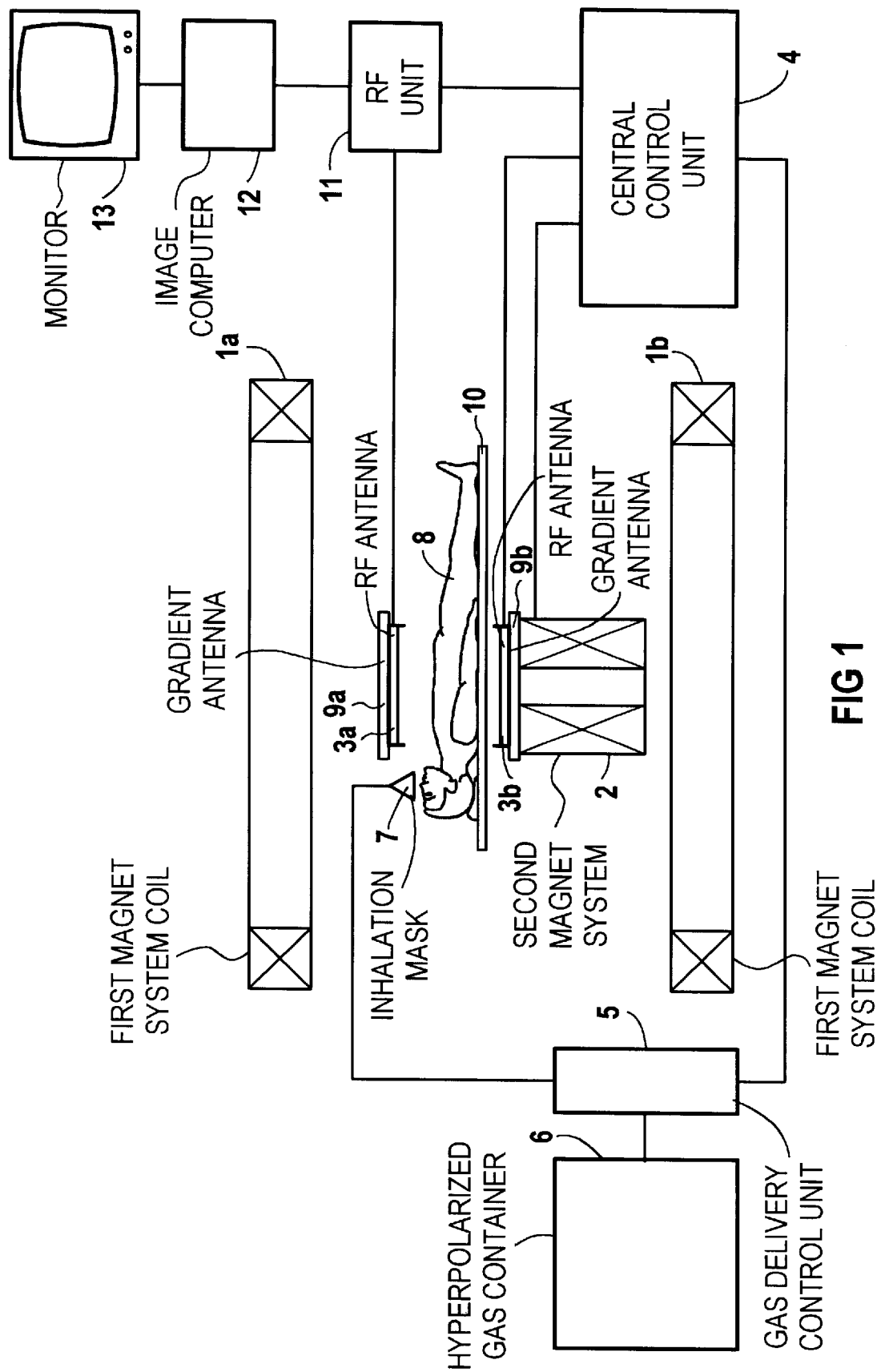
FIG. 1 schematically illustrates the magnetic resonance imaging structure of an overall installation constructed in accordance with the principles of the present invention.

In the arrangement shown in FIG. 1, a patient 8 lies on a support 10 disposed in a second magnet system is arranged composed of a Helmholtz coil pair 1a and 1b arranged at such a distance from each other so that unimpeded access to the patient 8 is possible. A first magnet system 2 lies under the patient 8. Further, gradient coils 9a and 9b and radio-frequency antennas 3a and 3b are arranged above and below the patient 8. Hyperpolarized gas that, as explained above, is generated by laser-induced optical pumping, is stored in a container 6. This hyperpolarized gas can be supplied to an inhalation mask 7 via a control unit 5 for gas delivery. The patient 8 can inhale the gas via the inhalation mask 7. The radio-frequency antenna 3a and 3b are connected to a radio-frequency unit 11 with which radio-frequency radiation can be emitted onto the patient 8, and with which nuclear magnetic resonance signals can also be received. The received nuclear magnetic resonance signals are converted by an image computer 12 into image information and are imaged on a monitor 13. The control unit for the gas delivery 5, and a power supply 4 for the first magnet system as well as for the radio-frequency unit 11 are operated by a central control unit 4.

For producing a standard proton image, a polarizing magnetic field is generated by brief-duration activation of the first magnet system 2 i.e., the nuclear spins in the patient 8 are aligned in the direction of the polarizing magnetic field. During the subsequent acquisition of the image data, only the magnet system 1 comprising coils 1a and 1b is activated, i.e., a low but uniform magnetic field takes effect. The nuclear spins are thereby excited by a radio-frequency field that is emitted to the antennas 3a and 3b. As warranted, a magnetic field gradient is produced with gradient coils 9a and 9b, so that the excitation of the nuclear spins is limited to one slice of the patient. A location coding is subsequently implemented in a known way with magnetic field gradients in various directions and an image that is displayed on a monitor 13 is reconstructed by the image computer 12 on the basis of the received nuclear magnetic resonance signals. The procedure of location coding and image reconstruction is not presented in greater detail herein since conventional methods can be used. Additionally or alternatively, an imaging can be implemented on the basis of inhaled, hyperpolarized gas; for example, the density distribution of protons is determined in a known way in the above-recited, first examination, and the distribution of the hyperpolarized gas in the patient 8 is determined in a second examination. Activation of the magnet system 2 is eliminated in the latter instance since the gas under observation is already optically polarized. Emission of the radio-frequency signals and reception of the radio-frequency signals ensues in the low magnetic field of the first magnet system with the resonant frequency of the hyperpolarized gas. Typically, $^{129}$Xe or $^{3}$He is employed as gas. One thus obtains two images with different diagnostic information. By selecting the time span between inhalation of the gas and examination, however, one can determine whether the gas distribution is to be viewed immediately after the inhalation or after absorption in the blood or in various organs.

The apparatus must thus be operated with two different frequencies. Antennas known as double-resonant antennas are employed for this purpose such as described, for example, in the references S. Sunder et al., "A Novel Double-Tuned Circuit For In Vivo NMR", Journal of Magnetic Resonance 74, 147–154 (1987), and R. D. Kendrice, "High Power $^{1}$H-$^{19}$F Excitation In A Multiple Resonance Signal Coil Circuit", Journal of Magnetic Resonance 75, 506–508 (1987).

Figure 2:
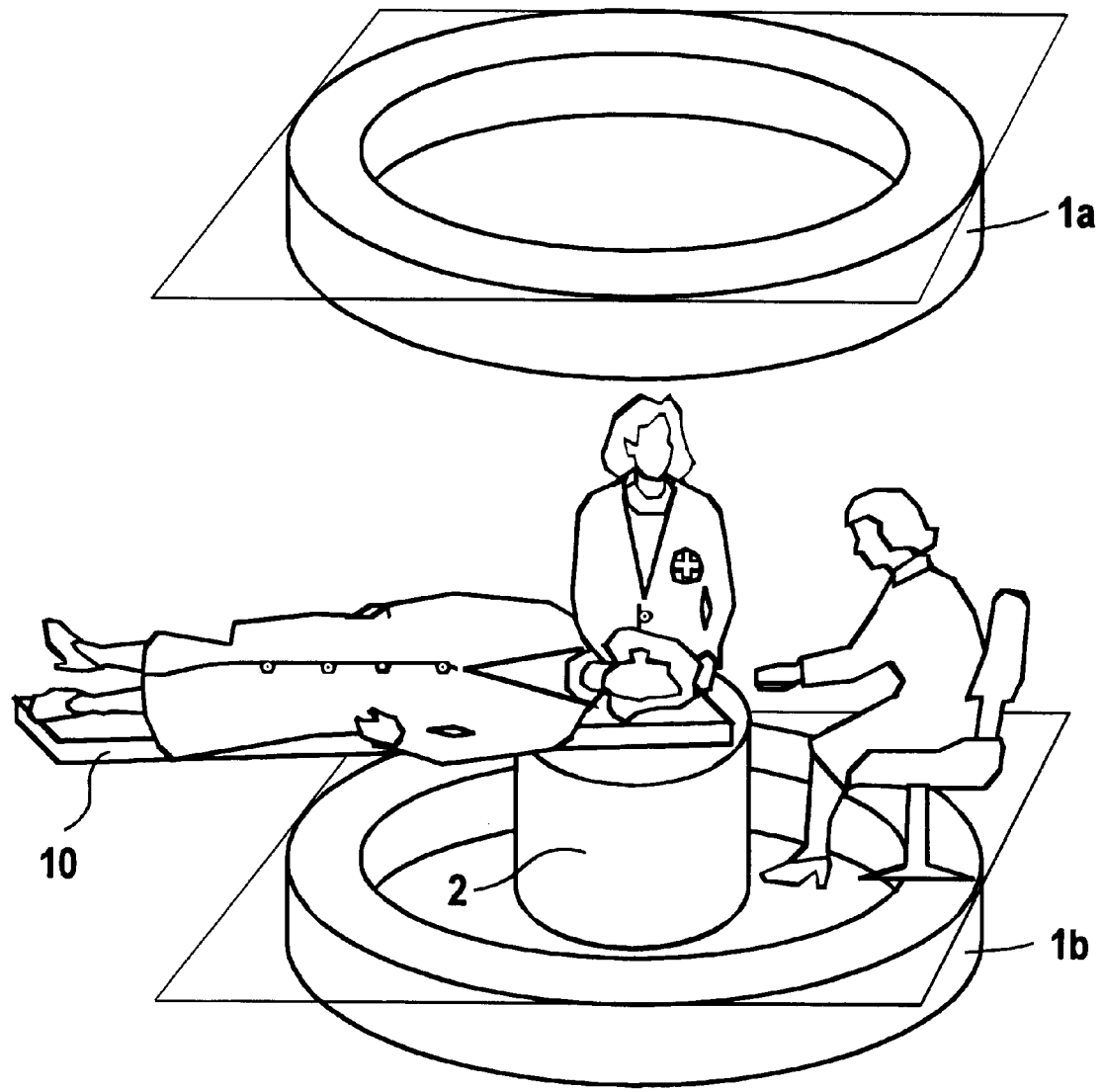
FIG. 2 schematically illustrates the structure of the magnet arrangement in the installation of FIG. 1.

FIG. 2 schematically shows the spatial arrangement of the two magnet systems required for the examination. The two coils 1a and 1b can be built into the floor and the ceiling of the examination room. The magnet 2 is arranged under the patient support 10. The patient 8 is thus accessible practically unimpeded for interventional applications. The gas supply means is not shown in FIG. 2 for clarity.

Expanded application possibilities are obtained due to the auxiliary components that enable an imaging with hyperpolarized gases. For example, blood vessels cannot be recognized well enough for operative interventions on the basis of proton images, however, it is precisely blood vessels that are imaged extremely well in the $^{129}$Xe image or $^{3}$He image given an appropriate waiting time after the inhalation. Cupping of the blood vessels can thus be reliably prevented in the operation. For example, in the inventive system used for proton imaging, for example, one can further obtain an image of the lung tissue and can obtain an image of the air volume by imaging with hyperpolarized gases.

The illustrated system having the relatively weak magnetic field in the read-out phase, however, also offers advantages given imaging exclusively with hyperpolarized gases. As a result of the low field strength, it is less expensive and can be built with significantly better accessability to the patient for the reasons that have already been set forth. The lower field strength does not influence the signal-to-noise ratio since this is no longer determined by the polarizing magnetic field, but instead by optical polarization.

Although modifications and changes may be suggested by those skilled in the art, it is the intention of the inventors to embody within the patent warranted hereon all changes and modifications as reasonably and properly come within the scope of their contribution to the art.

We claim as our invention:

1. A nuclear magnetic resonance tomography apparatus comprising:

a first magnet system which produces a magnetic field in a first examination volume having a first field strength for pre-polarizing nuclear spins in an examination subject disposed in said examination volume;

a second magnet system which produces a magnetic field in a second examination volume having a second field strength which is lower than first field strength;

gradient means for generating magnetic field gradients in said second examination volume;

radio frequency means for exciting nuclear spins in said examination subject and thereby producing nuclear magnetic resonance signals, and for reading out said nuclear magnetic resonance signals from said examination subject;

means for supplying a hyperpolarized gas to said examination subject; and control means for controlling said gradient means, said radio frequency means and said means for supplying a hyperpolarized gas for causing said radio frequency means to read out nuclear magnetic resonance signals of said hyperpolarized gas together with other nuclear magnetic resonance signals of said examination subject.

2. A nuclear magnetic resonance tomography apparatus as claimed in claim 1 wherein said other nuclear magnetic resonance signals include nuclear magnetic resonance signals at a proton resonant frequency, and wherein said nuclear magnetic resonant signals of said hyperpolarized gas have a further resonant frequency different from said proton resonant frequency, and wherein said radio frequency means includes a double-resonant antenna for said proton resonant frequency and said further resonant frequency.

3. A nuclear magnetic resonance tomography apparatus as claimed in claim 1 further comprising a support for said examination subject, and wherein said first magnetic system is disposed beneath said support.

4. A nuclear magnetic resonance tomography apparatus as claimed in claim 1 wherein said second magnet system comprises a Helmholtz arrangement having first and second coils respectively disposed above and below said examination subject at a spacing from each other allowing unimpeded access to said examination volume.

5. A nuclear magnetic resonance tomography apparatus as claimed in claim 4 for use in an examination room having a ceiling and a floor, and wherein said first coil is adapted for arrangement in the ceiling and said second coil is adapted for arrangement in the floor.

6. A nuclear magnetic resonance tomography apparatus as claimed in claim 1 wherein said means for suppling hyperpolarized gas comprises means for producing said hyperpolarized gas by laser-induced optical pumping and for delivering said hyperpolarized gas for inhalation to said examination subject.

7. A nuclear magnetic resonance tomography apparatus as claimed in claim 1 wherein said means for supplying a hyperpolarized gas comprises means for delivering said hyperpolarized gas for inhalation by said examination subject, and wherein said control means comprises means for allowing a time to pass after inhalation of said hyperpolarized gas by said examination subject and before controlling said radio frequency arrangement for exciting nuclear spins in said examination subject.

8. A nuclear magnetic resonance tomography apparatus as claimed in claim 1 wherein said means for supplying a hyperpolarized gas comprises means for supplying $^{129}$Xe as said hyperpolarized gas.

9. A nuclear magnetic resonance tomography apparatus as claimed in claim 1 wherein said means for supplying a hyperpolarized gas comprises means for supplying $^{3}$He as said hyperpolarized gas.

* * * * *